United States Patent [19]

Olsen

[11] Patent Number: 4,837,211

[45] Date of Patent: Jun. 6, 1989

[54] SPIRONOLACTONE COMPOSITION

[75] Inventor: James L. Olsen, Chapel Hill, N.C.

[73] Assignee: Carolina Medical Products, Inc., Chapel Hill, N.C.

[21] Appl. No.: 34,768

[22] Filed: Apr. 6, 1987

[51] Int. Cl.$^4$ .................. A61K 31/585; A61K 31/34; A61K 31/335

[52] U.S. Cl. ..................................... 514/175; 514/462

[58] Field of Search ................................ 514/462, 175

[56] References Cited

U.S. PATENT DOCUMENTS

| | | | |
|---|---|---|---|
| 4,108,982 | 8/1978 | Amschler | 514/380 |
| 4,195,084 | 3/1980 | Ong | 514/182 |
| 4,217,359 | 8/1980 | Krapcho | 514/423 |
| 4,502,989 | 3/1985 | Kamata et al. | 540/10 |
| 4,606,909 | 8/1986 | Bechgaard et al. | 424/481 |

*Primary Examiner*—Joseph L. Schofer
*Assistant Examiner*—Peter F. Kulkosky
*Attorney, Agent, or Firm*—Lynn E. Barber; Steven J. Hultquist

[57] ABSTRACT

A pharmaceutical composition, having utility as a diuretic or aldosterone antagonist, comprising spironolactone and an aqueous homogenizingly effective amount of a material selected from the group consisting of (i) sodium carboxymethylcellulose, and (ii) a mixture of methylcellulose and a dimethylpolysiloxane polymer.

Also disclosed is a method of diuretic or hyperaldosteronism treatment by administration of such composition, e.g., by oral administration.

18 Claims, No Drawings

SPIRONOLACTONE COMPOSITION

BACKGROUND OF THE INVENTION

1. Field of the Invention

This invention relates generally to pharmaceutical compositions having utility as diuretics and aldosterone antagonists, and specifically relates to spironolactone compositions of such type which are aqueously homogenizable in character.

2. Description of the Art

Spironolactone is a steroidal lactone compound having a significant aldosterone antagonistic character, which has been widely employed as a diuretic.

The structure and preparation of this compound are disclosed in U.S. Pat. No. 3,257,390 to A. A. Patchett.

Although spironolactone is a highly effective aldosterone antagonist, it has the instrinsic disadvantage that it is practically insoluble in water.

In instances where spironolactone has been employed in solid formulations for oral administration, it has been typical practice to utilize this compound in finely divided form, e.g., as a micronized powder, in tablets or capsules, which subsequent to ingestion are dispersed from the solid dosage form into the gastro-intestinal medium. Specifically, the micronized spironolactone powder has been utilized in such solid dosage forms as either compressed tablets or loose powders in capsules, to facilitate the bio-availability of this practically insoluble substance.

In the control of hyperaldosteronism, in infant or elderly individuals, such solid spironolactone dosage forms are highly disadvantageous. It would be a significant advance in the art to provide a liquid dosage form which is adaptable for oral administration to such infant or elderly individuals, susceptible to or suffering from hyperaldosteronism.

Accordingly, it is an object of the present invention to provide improved spironolactone dosage forms, either in the form of a solid powder composition which may be readily aqueously homogenized prior to ingestion, or else in the form of an aqueous spironolactone suspension.

It is another object of the invention to provide spironolactone formulations of such type which are readily formulated and easily administered by oral administration.

Other objects and advantages of the invention will be more fully apparent from the ensuing disclosure and appended claims.

SUMMARY OF THE INVENTION

The present invention broadly relates to a composition, useful as a diuretic or aldosterone antagonist, comprising spironolactone, and an aqueous homogenizingly effective amount of a material selected from the group consisting of (i) sodium carboxymethylcellulose, and (ii) a mixture of methycellulose and a dimethyl polysiloxane polymer.

Another aspect of the invention relates to a composition having utility as a diuretic or aldosterone antagonist, comprising from about 0.1 L to about 1.0 percent by weight spironolactone, from about 0.1 to about 2.0 percent by weight methylcellulose, from about 0.1 to about 1.0 percent by weight simethicone, from about 0.05 to about 0.5 percent by weight of a sweetener which does not affect the ionic strength of the composition, and from about 90.0 to about 99.0 percent by weight water.

A further aspect of the invention relates to a method of diuretic treatment of a mammal, comprising administering to such mammal a diuretically effective amount of a composition as above described.

In a still further aspect, the present invention relates to a method of hyperaldosteronism treatment, comprising administering to a mammal an aldosterone antagonistically effective amount of a composition as above described.

DETAILED DESCRIPTION OF THE INVENTION AND PREFERRED EMBODIMENTS THEREOF

The present invention is based on the surprising and unexpectd discovery that the practically insoluble character of spironolactone in water may be largely overcome in the provision of a spironolactone composition which is aqueously homogenizable, i.e., in the presence of water or other aqueous medium forms a highly uniform suspension of the active ingredient without a high incidence of foaming.

A characteristic of spironolactone per se which appears to have hindered its utilization in liquid dosage forms is its tendency to substantially foam in water or other aqueous media when it is attempted to disperse the active ingredient therein. Such foaming is severely detrimental to the bioavailability of the spironolactone in vivo.

Such deficiency of spironolactone has been overcome in accordance with the present invention by utilizing spironolactone in admixture with either sodium carboxymethylcellulose, or in admixture with both methylcellulose and a dimethylpolysiloxane polymer. Each of these alternative embodiments of the invention evidences the surprising characteristic of being readily homogenized with low foaming in aqueous medium.

The use of sodium carboxymethycellulose as an aqueous homogenizingly effectively additive for spironolactone is very surprising in view of the fact that such material is typically employed in the pharmaceutical industry as a suspending agent, tablet excipient, or viscosity increasing agent, most frequently in the later role, as a thickener. One of ordinary skill would not logically seek to add a thickener to a foaming material, since it would be expected that the foaming activity would thereby be exacerbated. In contrast to such anticipated behavior, it is found that the sodium carboxymethycellulose in combination with spironolactone wholly supresses the formation of foam when used in concentrations effective to provide thickening and suspension of the spironolactone active ingredient in aqueous medium.

The alternative embodiment, in which spironolactone is used with an aqueous homogenizingly effective mixture of methylcellulose and a dimethylpolysiloxane polymer, also evidences a surprising and unexpected character. As mentioned, spironolactone per se in water or other aqueous medium exhibits substantial foaming activity. In addition, spironolactone alone is practically insoluble in water and does not disperse well. Although methylcellulose is commonly used in the pharmaceutical industry as a suspending agent in aqueous pharmaceutical compositions, it would logically be expected by one of ordinary skill of the art that the addition of such suspending agent would, in the same manner as discussed above with respect to sodium carboxymethylcellulose, exacerbate the foaming problem to such an extent that foaming could not be controlled by addition of reasonably low levels of pharmaceutically acceptable anti-foaming agents. This expectation is buttressed by the fact that addition of methylcellulose to spironolactone in water results in the generation of excessive foam. Surprisingly, however, when methylcellulose and a dimethylpolysiloxane polymer (as a pharmaceutically acceptable anti-foam material) are added to spironolactone, the resulting mixture is readily aqueously homogenizable with no significant evidence of any foaming behavior.

As used herein, spironolactone refers to the compound 7-(acetylthio)-17-hydroxy-3-oxo-pregn-4-ene-21-carboxylic acid-gamma-lactone. The spironolactone may be used in the present invention in its typical form of a crystalline solid, which preferably is finely divided, as in the form of a micronized powder having an average particle size of from about 0.5 to about 5 microns, and preferably approximately 1.0 micron.

The sodium carboxymethylcellulose which is useful in combination with the spironolactone to provide an aqueously homogenizable, low foaming composition is suitably employed in its typical form of a granular solid, in an amount which is suspendingly and anti-foamingly effective for the spironolactone in the composition.

The sodium carboxymethylcellulose and spironolactone thus may be provided as a suitable solid admixture which is dispersible into water at the point of dispensing, e.g., by a pharmacist, to yield an aqueous spironolactone composition which is suitable for oral administration.

A generalized formulation of spironolactone and sodium carboxymethylcellulose comprises from about 5 to 95 percent by weight spironolactone, and from about 10 to about 95 percent by weight sodium carboxymethylcellulose, based on the total weight of the spironolactone and sodium carboxymethylcellulose. Such solid mixture then may be dispersed into water in suitable quantity to provide a liquid spironolactone composition containing from about 0.1 to 1.0 percent by weight spironolactone, based on the total weight of the liquid composition.

In the alternative embodiment of the invention, wherein methylcellulose is employed in combination with a polysiloxane polymer and spironolactone, the methylcellulose material may suitably be a pharmaceutically pure grade of crystalline methylcellulose, in particulate form, e.g., as is available under the trademark "METHOCEL" from The Dow Chemical Co., Midland, Mich. with methylcellulose and spironolactone, may suitably have the formula set forth below:

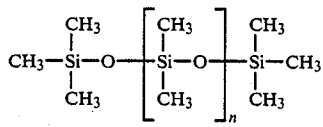

ps wherein n is from about 200 to about 350. Such polymer may suitably be provided as a mixture of dimethyl polysiloxanes of such type and silica gel which has been purified for pharmaceutical use. A particularly preferred dimethyl polysiloxane/silica gel mixture is simethicone, commercially available under the trade name "Medical Antifoam A" from Dow-Corning, Midland, Mich. Another useful simethicone material is "Medical Antifoam AF Emulsion" (Simethicone Emulsion USP), a 30 percent emulsion of simethicone available from the same manufacturer.

The foregoing composition comprising spironolactone, methylcellulose, and a dimethylpolysiloxane polymer may suitably be provided as a solid powder mixture, which when added to water is readily aqueously homogenizable with little or no foam formation. Broadly, compositions of such type may contain from about 3.0 to about 90.0 percent by weight spironolactone, from about 5.0 to about 90.0 percent by weight methylcellulose, and from about 0.3 to about 50.0 percent by weight of dimethylpolysiloxane polymer. This solid mixture may then be added to a suitable amount of water to provide spironolactone in an aqueously dispersed form, at a concentration of from about 0.1 to about 1.0 percent by weight, as suitable for oral administration.

The above-described embodiments of the spironolactone composition of the invention in water or other aqueous medium, as a formulation for oral administration, may suitably comprise any additives which are necessary or desirable in the specific application, and which do not preclude the efficacy of the spironolactone active ingredient for its intended purpose.

Examples of such additives include preservatives such as antibiotics effective to suppress formation of molds and bacteria in the formulation, fillers of various types, flavors, coloring additives, and sweeteners, etc. In this respect, it is to be noted that the "basic" compositions, either (a) a composition comprising spironolactone, and sodium carboxymethylcellulose, optionally in water medium, or (b) spironolactone, methylcellulose, and a dimethylpolysiloxane polymer, optionally in water medium, are of essentially neutral pH, generally being of a pH in the range of from about 7 to 8, and are isotonic, having an ionic strength generally equal to that of ambient body fluids, in the in vivo environment after oral administration.

Such isotonic character is a highly important feature with regard to the suitability of the compositions of the invention in application to infants and elderly individuals, particularly in infants, since any deviation from isotonicity will typically cause significant diarrhea in infants.

In order to maintain the aforementioned isotonicity of the spironolactone composition, it is essential that the aforementioned optional additives do not significantly change the ionic strength of the composition. For example, with reference to optional sweetener additives, it is important to utilize non-sucrose sweeteners, since sucrose will destroy the isotonicity of the composition. Accordingly, artificial sweeteners such as sodium saccharin, and sweeteners available under the trademarks NutraSweet®, and Magnasweet®, are preferred, since such artificial sweeteners do not significantly effect the isotonicity of the composition.

Illustrative of a suitable spironolactone composition comprising optional additives of the aforementioned type, in an aqueous syrup dosage form, is the following formulation:

| COMPONENT | CONCENTRATION |
| --- | --- |
| Spironolactone | 5.0 grams |
| Sorbic Acid (Preservative) | 0.5 grams |
| Potassium Sorbate (Preservative) | 2.0 grams |
| Simethicone | 0.67 gram |
| Sodium Saccharin | 1.35 grams |
| Methylcellulose | 12.0 grams |

| -continued | |
|---|---|
| COMPONENT | CONCENTRATION |
| 4% Magnasweet ®/Glycerin | 14.0 milliliters |
| Banana Flavor | 1.0 milliliter |
| Purified Water Q.S. AD | 1.0 liter |

A significant advantage of the liquid dosage form spironolactone compositions of the invention is that same are absorbable at a higher rate and to a greater extent than the solid dosage form spironolactone compositions which have been available to date. The reason for this is that the solid dosage form compositions require dispersion and subsequent dissolution of the spironolactone in vivo, whereas the spironolactone liquid dosage forms of the present invention are already provided in aqueous suspension, thereby maximizing their bioavailability, and resulting in the aforementioned increased rate and extent of absorption.

The features and advantages of the present invention are more fully shown with respect to the following non-limiting examples, wherein all parts and percentages are by weight, unless otherwise expressly stated.

EXAMPLE I 50 milligrams of spironolactone in solid micronized crystalline form was added to 10 milliliters of water in a 10 milliliter bottle having an internal diameter of 2 cm and a height of 5 cm, and shaken to effect dispersion of the spironolactone in the aqueous medium. Following vigorous shaking, the spironolactone remained poorly dispersed, and generated significant foam, on the order of ⅛ to ¼ inch above the water surface.

EXAMPLE II 50 milligrams of spironolactone was added to 10 milliliters of water in a bottle of the type used in Example I, followed by addition of 120 milligrams of methylcellulose. This aqueous composition was vigorously shaken, resulting in improved dispersion of the spironolactone relative to Example I, but with attendant generation of extensive foam. The body of foam above the water surface was approximately ½ inch in height.

EXAMPLE III

To the aqueous dispersion of Example II was added 6.7 milligrams of simethicone. After vigorous shaking, the composition was translucent in character, and exhibited good viscosity and suspension characteristics, without any evidence of foam.

EXAMPLE IV 50 milligrams of spironolactone was added to 10 milliliters of water in a bottle of the type used in Example I, followed by addition of 120 milligrams of sodium carboxymethylcellulose. The resulting mixture was shaken vigorously. After shaking, the mixture was uniformly dispersed, with good viscosity and suspension characteristics, a substantially neutral pH (approximately 7.0), and no foam on the liquid surface.

EXAMPLE V

A spironolactone composition in accordance with the invention was made up, having the composition shown in Table II below.

TABLE II

| COMPONENT | CONCENTRATION |
|---|---|
| Spironolactone | 5.0 grams |
| Sorbic Acid | 0.5 grams |
| Potassium Sorbate | 2.0 grams |
| Simethicone | 0.67 grams |
| Sodium Saccharin | 1.35 grams |
| Methylcellulose | 12.0 grams |
| 4% Magnasweet ®/Glycerin | 14.0 milliliters |
| Banana Flavor | 1.0 milliliter |
| Purified Water q.s. ad | 1.0 liter |

The resulting composition was homogeneous in character, with good suspension and viscosity characteristics, and no foam present therein. This composition had a neutral pH (7-8) and was isotonic.

This formulation was tested for stability at a temperature of 37° C., against a control sample of the formulation at room temperature. Corresponding amounts of material were taken from the respective samples at monthly intervals and analyzed by HPLC assays to assess their stability. After three months, both the elevated temperature sample and the control sample were found to be fully stable.

EXAMPLE VI

A comparative dissolution study was conducted on commercially available solid spironolactone tablets (Aldactone ®, G. D. Searle & Company) in two separate runs (Sample 1 and Sample 2), a generic solid spironolactone tablet (Rugby, Inc., Rockville Center, NY) (Sample 3), and an aqueous suspension of spironolactone prepared according to the procedure of Example V (Sample 4).

The study was carried out using a USP Dissolution Apparatus 3 (p. 959, USP XX (1980)) with a slightly acidic aqueous solution of 0.04N HCl in Purified Water as the dissolution medium, at a temperature of 37 degrees Centigrade.

In each test, a sample in the dissolution medium was added to the apparatus, and the apparatus then turned on.

At various intervals, corresponding amounts of the dissolution medium containing the respective samples were withdrawn, filtered, and injected into a Waters Reverse Phase HPLC (High Pressure Liquid Chromatograph) L1 Column (Waters Chromatography Division of Millipore Corporation, Milford, Mass.), calibrated with a standard containing 10 micrograms spironolactone per milliliter of solution and having a mean peak area of 0.420. Flow rates in the respective runs of Samples 1–4 were each 1 milliliter per minute. In this manner the spironolactone in the respective Samples 1–4 was separated and quantified. Results are given below in Table I, in micrograms of spironolactone per milliliter of eluate.

TABLE I

| Micrograms of Spironolactone per Milliliter of Eluate, for: | Elapsed Elutriation Time, Minutes | | | | | |
|---|---|---|---|---|---|---|
| | 1 | 3 | 5 | 10 | 15 | 20 |
| Sample 1 | .48 | .88 | 2.5 | 7.1 | 8.8 | 9.5 |
| Sample 2 | .83 | 1.1 | 4.7 | 8.9 | — | — |
| Sample 3 | .44 | 1.5 | 3.1 | 5.2 | — | — |
| Sample 4 | 2.6 | 5.3 | 6.9 | 8.9 | — | — |

As shown by the data in Table I, the aqueous suspension of Sample 4 gave very high initial eluate concentrations due to the uniform homogeneous suspension thereby achieved, as compared to the commercial solid tablets of Samples 1-3. These data indicate that the spironolactone dosage form of the present invention is significantly more quickly and extensively bioavailable than the commercially available solid dosage forms which were tested.

While preferred embodiments of the invention have been shown and described in detail, it will be appreciated that other variations, modifications, and embodiments are possible, and all such variations, modifications, and embodiments are therefore to be regarded as being within the spirit and scope of the invention.

What is claimed is:

1. A pharmaceutical spironolactone composition devoid of chelating agents, which composition is of improved aqueous dispersability and has low amounts of foam, providing a spironolactone liquid dosage form for oral administration having utility as a diuretic or aldosterone antagonist, said composition comprising:
   (a) spironolactone; and
   (b) an aqueous homogenizingly effective amount of a mixture of:
       methylcellulose, and
       a dimethylpolysiloxane polymer, said dimethylpolysiloxane polymer having the formula:

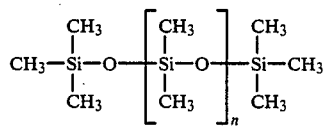

wherein n is from about 200 to about 350;
wherein spironolactone is the only active ingredient, wherein constituents (a) and (b) are not combined with one another in controlled release multiple units, and wherein said constituents are devoid of an erodable coating.

2. A composition according to claim 1, comprising the spironolactone in the form of a micronized powder.

3. A composition according to claim 1, having a substantially neutral pH.

4. An aqueous suspension of a composition according to claim 1.

5. A composition according to claim 1, wherein the spironolactone is micronized, having an average particle size in the range from about 0.5 to about 5 microns.

6. A pharmaceutical spironolactone composition devoid of chelating agents, which composition is of improved aqueous dispersability and has low amounts of foam, providing a spironolactone liquid dosage form for oral administration having utility as a diuretic or aldosterone antagonist, said composition comprising:
   (a) from about 3 to about 90 percent by weight of spironolactone; and
   (b) from about 5 to about 90 percent by weight of methylcellulose; and
   (c) from about 0.3 to about 50 percent by weight of a dimethylpolysiloxane polymer, said dimethylpolysiloxane polymer having the formula:

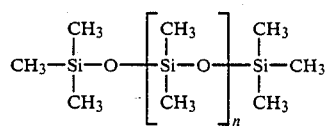

wherein n is from about 200 to about 350;
wherein spironolactone is the only active ingredient, wherein constituents (a), (b), and (c) are not combined with one another in controlled release multiple units, and wherein said constituents are devoid of an erodable coating.

7. A composition according to claim 6 wherein said dimethylpolysiloxane polymer is present in admixture with a pharmaceutically acceptable silica gel.

8. A pharmaceutical spironolactone liquid dosage form pharmaceutical composition of improved aqueous dispersability and having low amounts of foam, devoid of chelating agents, and having utility as a diuretic or aldosterone antagonist, comprising:
   (a) from about 0.1 to about 1.0 percent by weight spironolactone;
   (b) from about 0.1 to about 2.0 percent by weight methylcellulose;
   (c) from about 0.01 to about 1.0 percent by weight simethicone;
   (d) from about 0.05 to about 0.5 percent by weight of a sweetener which does not significantly affect the ionic strength of the composition; and
   (f) from about 90 to about 99 percent by weight water; wherein spironolactone is the only active ingredient.

9. A composition according to claim 8 wherein said sweetener is a non-sucrose sweetener.

10. A composition according to claim 8, having a pH in the range of from about 7 to about 8.

11. A composition according to claim 8, which is isotonic in character.

12. A composition according to claim 8, comprising from about 0.1 to 0.5 percent by weight of a preservative for said composition.

13. A method of diuretic treatment of a mammal, comprising administering to said mammal an aqueous dispersion of a diuretically effective amount of a composition according to claim 1.

14. A method according to claim 13, wherein said mammal is a human.

15. A method according to claim 13, wherein said aqueous dispersion is orally administered.

16. A method of hyperaldosteronism treatment, comprising administering to a mammal an aqueous dispersion of an aldosterone antagonistically effective amount of a composition according to claim 1.

17. A method according to claim 16, wherein said mammal is a human.

18. A method according to claim 16, wherein said aqueous dispersion is orally administered.

* * * * *